(12) United States Patent
Downey et al.

(10) Patent No.: US 8,823,510 B2
(45) Date of Patent: *Sep. 2, 2014

(54) SYSTEMS AND METHODS FOR WIRELESSLY PROGRAMMING A PRESCRIPTION BOTTLE CAP

(75) Inventors: Laura A. Downey, West Lafayette, IN (US); Steven J. Klink, Lafayette, IN (US); Jonathan Bautista Labayo, Terre Haute, IN (US); Virginie Agathe Frizon-Hubert, West Bloomfield, MI (US); Matthew Oran Moore, Lexington, SC (US); Jessica Louise Palmer, Troy, MI (US); Matthew Robert Runchey, Springboro, OH (US)

(73) Assignee: KlinDown, LLC, West Lafayette, IN (US)

( * ) Notice: Subject to any disclaimer, the term of this patent is extended or adjusted under 35 U.S.C. 154(b) by 481 days.

This patent is subject to a terminal disclaimer.

(21) Appl. No.: 12/978,013

(22) Filed: Dec. 23, 2010

(65) Prior Publication Data

US 2012/0163132 A1 Jun. 28, 2012

(51) Int. Cl.
*G08B 1/08* (2006.01)
*A61J 7/04* (2006.01)
*A61J 1/14* (2006.01)
*G06F 19/00* (2011.01)

(52) U.S. Cl.
CPC ............ *A61J 1/1412* (2013.01); *A61J 2200/30* (2013.01); *A61J 7/0409* (2013.01); *G06F 19/3462* (2013.01); *A61J 7/0481* (2013.01)
USPC .............. 340/539.12; 340/539.13; 340/572.1; 340/573.1; 340/10.1; 340/309.16; 215/228; 221/1

(58) Field of Classification Search
None
See application file for complete search history.

(56) References Cited

U.S. PATENT DOCUMENTS

| 927,007 | A | | 7/1909 | Scritchfield |
|---|---|---|---|---|
| 2,853,182 | A | | 9/1958 | Barnett |
| 4,361,408 | A | | 11/1982 | Wirtschafter |
| 4,367,955 | A | | 1/1983 | Ballew |
| 4,419,016 | A | * | 12/1983 | Zoltan .............................. 368/10 |

(Continued)

FOREIGN PATENT DOCUMENTS

| EP | 1811715 | 7/2007 |
|---|---|---|
| WO | WO 2010/069061 | 8/2010 |

OTHER PUBLICATIONS

Notice of Allowance from U.S. Appl. No. 12/978,004, dated Apr. 15, 2013, 11 pages.

(Continued)

*Primary Examiner* — Curtis King
(74) *Attorney, Agent, or Firm* — Sterne, Kessler, Goldstein & Fox P.L.L.C.

(57) ABSTRACT

Embodiments of the present invention provide systems and methods for wirelessly programming a prescription bottle cap. In an embodiment, the system includes a base station comprising an inductor and processor configured to receive prescription dosage instructions and instruct the inductor to alter a magnetic field in a manner representative of the prescription dosage instructions. In an embodiment, the system further includes a wirelessly programmable cap comprising a sensor configured to detect the magnetic field and to generate the prescription dosage information based on the magnetic field. A control unit is configured to instruct the wirelessly programmable cap to send an alert at a time designated by the prescription dosage information.

20 Claims, 7 Drawing Sheets

(56) References Cited

U.S. PATENT DOCUMENTS

| | | | |
|---|---|---|---|
| 4,504,153 A * | 3/1985 | Schollmeyer et al. | 368/10 |
| 4,616,316 A | 10/1986 | Hanpeter et al. | |
| 4,837,719 A | 6/1989 | McIntosh et al. | |
| 4,849,948 A | 7/1989 | Davis et al. | |
| 4,911,327 A | 3/1990 | Shepherd et al. | |
| 4,939,705 A | 7/1990 | Hamilton et al. | |
| 4,984,295 A | 1/1991 | Engstrom et al. | |
| 5,007,649 A | 4/1991 | Richardson | |
| 5,016,230 A | 5/1991 | Seifers et al. | |
| 5,020,037 A | 5/1991 | Raven | |
| 5,054,787 A | 10/1991 | Richardson | |
| 5,233,571 A | 8/1993 | Wirtschafter | |
| 5,239,491 A | 8/1993 | Mucciacciaro | |
| 5,313,439 A | 5/1994 | Albeck | |
| 5,408,443 A | 4/1995 | Weinberger | |
| 5,586,087 A | 12/1996 | Silverson | |
| 5,625,334 A | 4/1997 | Compton | |
| 5,706,257 A | 1/1998 | Rothman et al. | |
| 5,751,661 A | 5/1998 | Walters | |
| 5,852,590 A | 12/1998 | de la Huerga | |
| 5,953,288 A | 9/1999 | Chappell | |
| 5,983,182 A | 11/1999 | Moore | |
| 6,084,504 A | 7/2000 | Rosche et al. | |
| 6,088,448 A | 7/2000 | Poirel | |
| 6,229,431 B1 | 5/2001 | Weiner | |
| 6,259,654 B1 | 7/2001 | de la Huerga | |
| 6,294,999 B1 | 9/2001 | Yarin et al. | |
| 6,317,390 B1 | 11/2001 | Cardoza | |
| 6,324,123 B1 | 11/2001 | Durso | |
| 6,373,786 B1 | 4/2002 | Kagan et al. | |
| 6,373,787 B1 | 4/2002 | Breimesser et al. | |
| 6,380,858 B1 | 4/2002 | Yarin et al. | |
| 6,401,991 B1 | 6/2002 | Eannone | |
| 6,424,599 B1 | 7/2002 | Ditzig | |
| 6,441,722 B2 | 8/2002 | Weiner | |
| 6,529,446 B1 | 3/2003 | de la Huerga | |
| 6,545,592 B2 | 4/2003 | Weiner | |
| 6,604,650 B2 | 8/2003 | Sagar | |
| 6,633,796 B1 | 10/2003 | Pool et al. | |
| 6,667,936 B1 | 12/2003 | Ditzig | |
| 6,707,763 B2 | 3/2004 | Osberg et al. | |
| 6,710,703 B2 | 3/2004 | Huang | |
| 6,751,730 B1 | 6/2004 | Walker et al. | |
| 6,845,064 B2 | 1/2005 | Hildebrandt | |
| 6,859,136 B2 | 2/2005 | Gastel | |
| 7,061,831 B2 | 6/2006 | De La Huerga | |
| 7,081,807 B2 | 7/2006 | Lai | |
| 7,138,906 B2 | 11/2006 | Rosche | |
| 7,212,100 B2 | 5/2007 | Terenna | |
| 7,230,521 B2 | 6/2007 | Terenna | |
| 7,259,710 B2 | 8/2007 | Kisliakov | |
| 7,304,913 B2 | 12/2007 | Niemiec et al. | |
| 7,362,660 B2 | 4/2008 | Hildebrandt | |
| 7,382,692 B1 | 6/2008 | Hildebrandt | |
| 7,408,843 B2 | 8/2008 | Brandon | |
| 7,719,927 B1 * | 5/2010 | Robinson et al. | 368/10 |
| 7,844,361 B2 | 11/2010 | Jean-Pierre | |
| 8,102,735 B2 * | 1/2012 | Morse | 368/10 |
| 2001/0022758 A1 | 9/2001 | Howard | |
| 2001/0028308 A1 | 10/2001 | De La Huerga | |
| 2003/0063522 A1 | 4/2003 | Sagar | |
| 2003/0086338 A1 | 5/2003 | Sastry et al. | |
| 2003/0099157 A1 | 5/2003 | Quine | |
| 2003/0099158 A1 | 5/2003 | De La Huerga | |
| 2003/0198134 A1 | 10/2003 | Hildebrandt | |
| 2004/0075642 A1 | 4/2004 | Kisliakov | |
| 2004/0179430 A1 | 9/2004 | Bahar et al. | |
| 2004/0246819 A1 | 12/2004 | Quine | |
| 2005/0117455 A1 | 6/2005 | Valerio | |
| 2006/0152367 A1 * | 7/2006 | Narayanaswamy | 340/572.1 |
| 2006/0220818 A1 | 10/2006 | Trochesset | |
| 2006/0280035 A1 | 12/2006 | Walker et al. | |
| 2006/0285441 A1 | 12/2006 | Walker et al. | |
| 2007/0001668 A1 | 1/2007 | Mock et al. | |
| 2007/0097792 A1 | 5/2007 | Burrows et al. | |
| 2007/0132581 A1 | 6/2007 | Molyneaux et al. | |
| 2007/0173971 A1 * | 7/2007 | Richardson et al. | 700/231 |
| 2007/0292812 A1 * | 12/2007 | Furner et al. | 431/289 |
| 2008/0027291 A1 | 1/2008 | Williams-Hartman | |
| 2008/0114490 A1 | 5/2008 | Jean-Pierre | |
| 2008/0162188 A1 * | 7/2008 | Kripalani et al. | 705/3 |
| 2008/0165623 A1 | 7/2008 | Morse | |
| 2009/0009300 A1 * | 1/2009 | Jarvis et al. | 340/309.16 |
| 2010/0102955 A1 * | 4/2010 | Choi et al. | 340/539.12 |
| 2010/0249881 A1 | 9/2010 | Corndorf | |
| 2010/0270257 A1 | 10/2010 | Wachman et al. | |
| 2011/0069587 A1 * | 3/2011 | Brandon | 368/10 |
| 2011/0226817 A1 * | 9/2011 | Ortenzi et al. | 222/424.5 |
| 2011/0284415 A1 * | 11/2011 | Balakier et al. | 206/459.1 |
| 2012/0160908 A1 | 6/2012 | Downey et al. | |
| 2012/0161929 A1 | 6/2012 | Downey et al. | |

OTHER PUBLICATIONS

Invitation to Pay Additional fees and Partial International Search Report for PCT/US2011/065787, dated Jun. 6, 2012, 4 pages.
The Pill Timer, as archived by web.archive.org on or before 2014, 10 pages.
e-pill Multi-Alarm TimeCap, copyright 1997-2012, 13 pages.
Non-Final Office Action from U.S. Appl. No. 12/978,004, dated Mar. 27, 2012, 14 pages.
Non-Final Office Action from U.S. Appl. No. 12/978,010, dated Nov. 21, 2012, 14 pages.
Final Office Action from U.S. Appl. No. 12/978,004, dated Nov. 26, 2012, 20 pages.
Non-Final Office Action from U.S. Appl. No. 12/978,004, dated Mar. 14, 2013, 16 pages.

* cited by examiner

SYSTEMS AND METHODS FOR WIRELESSLY PROGRAMMING A PRESCRIPTION BOTTLE CAP

FIELD OF THE INVENTION

This field relates to caps and data transfer.

BACKGROUND OF THE INVENTION

Poor adherence to medication is a large problem in the United States and around the world. Patients reminded to take medications have an overall higher adherence rate than control groups.

However, current adherence systems require complicated programming, have a high cost, and/or are non-portable. Further, current adherence systems do not effectively enable support from a health care provider, such as a doctor or pharmacist. Additionally, few current adherence systems are marketed and sold as part of the original packaging for medication.

What is needed are inexpensive, efficient systems and methods to assist patients in adherence to prescribed medication.

BRIEF SUMMARY OF THE INVENTION

This section is for the purpose of summarizing some aspects of the present invention and to briefly introduce some embodiments. Simplifications or omissions may be made to avoid obscuring the purpose of the section. Such simplifications or omissions are not intended to limit the scope of the present invention.

Embodiments of the present invention provide systems and methods for wirelessly programming a prescription bottle cap. In an embodiment, the system includes a base station comprising an inductor and processor configured to receive prescription dosage instructions and instruct the inductor to alter a magnetic field in a manner representative of the prescription dosage instructions. In an embodiment, the system further includes a wirelessly programmable cap comprising a sensor configured to detect the magnetic field and to generate the prescription dosage information based on the magnetic field. A control unit is configured to instruct the wirelessly programmable cap to send an alert at a time designated by the prescription dosage information.

Further features and advantages of the invention, as well as the structure and operation of various embodiments of the present invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated in and constitute part of the specification, illustrate embodiments of the invention and, together with the general description given above and the detailed descriptions of embodiments given below, serve to explain the principles of the present invention. In the drawings.

Figure 1:
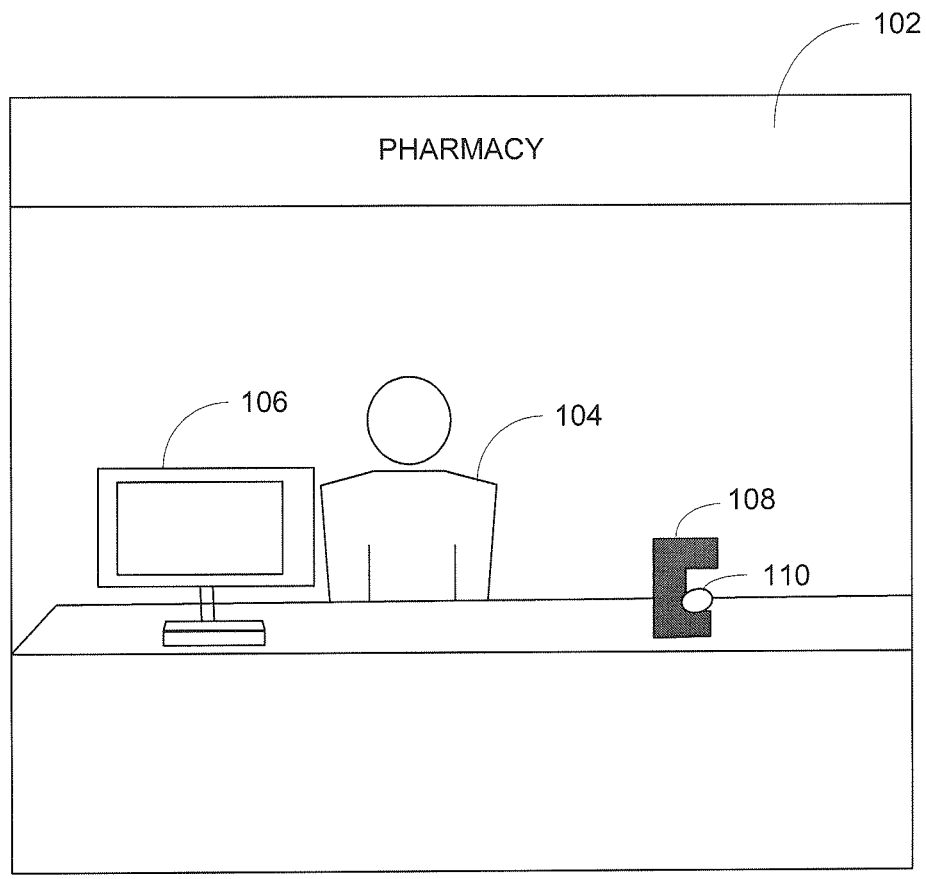
FIG. 1 is a diagram of a system in accordance with an embodiment of the present invention.

Features and advantages of the present invention will become more apparent from the detailed description set forth below when taken in conjunction with the drawings, in which like reference characters identify corresponding elements throughout. In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

1. Overview

The National Council on Patient Information and Education (NCPIE) stated in a 2007 report that "poor adherence with medication regimens has reached crisis proportions in the United States and around the world." The World Health Organization (WHO) projects that 50 percent of patients take their medications as prescribed. Medication non-adherence leads to unnecessary disease progression and complications, reduced functional abilities, a lower quality of life, and premature death.

Reasons for poor medication adherence include forgetfulness, lack of access to medication, problems with medication, poor understanding of the dosing instructions and/or the need for adherence. High adherence is generally associated with better treatment outcomes and lower healthcare costs. A general correlation exists between treatment response and adherence to the dose and schedule of a therapy. However, few adherence intervention strategies have proven simple and affordable enough to be both effective and sustainable over the long term.

Systems and methods are disclosed for providing an inexpensive, disposable, wirelessly programmable cap for pharmaceuticals. In an embodiment, the cap is configured to remind a patient when medication is due to be taken (using, for example, a visual or audio reminder). The cap records patient dosing history when the cap is open and transmits the dosing history to the Internet or a local program to capture dosing information to be later shared with the pharmacy, physicians, insurance company, and/or caregivers. The cap is advantageously wirelessly programmable from a pharmacy database system (using, for example, pharmacy records containing doctor prescribed dosing information) for each prescription and thus requires no manual programming by a pharmacist.

Additionally, systems in accordance with the present invention may communicate a reminder to a PDA or phone to send a text message to a patient to remind the patient when medication is due to be taken. Embodiments of the present invention are small and easily portable and adaptable to standard prescription vials and mail order bottles. Further, embodiments of the cap are designed to be adaptable to incorporate safety cap features.

2. Embodiments

FIG. 1 is a diagram of a system 100 at a pharmacy 102 in accordance with an embodiment of the present invention. In FIG. 1, a pharmacist 104 enters prescription information into a computer 106 and begins to fill a prescription. Pharmacist 104 scans the barcode from a prescription label, and a prescription ID is sent to computer 106. Software running on computer 106 accesses a database of prescription information, including SIG codes, associated with the identifier. In an embodiment, the software decodes the SIG codes into standard English (for example, "2x/day" may be decoded to "two times per day").

Pharmacist 104 then uses a base station accessible by computer 106 to program a wirelessly programmable cap 110. For example, pharmacist 104 may program cap 110 by placing it on or near base station 108. The translated prescription information is then transmitted from computer 106 to base station 108 (for example, through a Universal Serial Bus (USB) cable) to program cap 110.

Figure 2:
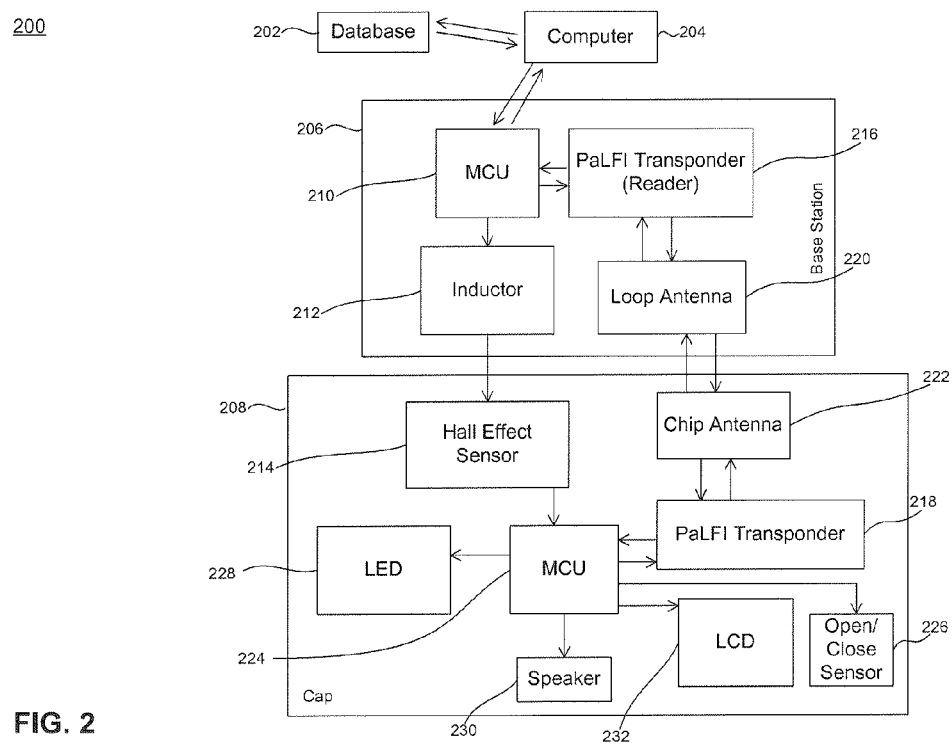
FIG. 2 is a block diagram of a system in accordance with an embodiment of the present invention.

FIG. 2 shows a block diagram of a system 200 in accordance with an embodiment of the present invention. In FIG. 2, a database 202 stores pharmacy records including doctor prescribed dosing information. Database 202 is accessible via a computer 204. A base station 206 is connected to (or in wireless communication with) computer 204. In an embodiment, base station 206 is connected to computer 204 using a USB cable, which may also be used to power base station 204. Base station 204 is configured to transmit information to and receive information from a wirelessly programmable cap 208.

FIG. 2 shows a block diagram of a system 200 in accordance with an embodiment of the present invention. In FIG. 2, a database 202 stores pharmacy records including doctor prescribed dosing information. Database 202 is accessible via a computer 204. A base station 206 is connected to (or in wireless communication with) computer 204. In an embodiment, base station 206 is connected to computer 204 using a USB cable, which may also be used to power base station 206. Base station 206 is configured to transmit information to and receive information from a wirelessly programmable cap 208.

In an embodiment, base station 206 includes a microcontroller unit (MCU) 210, such as the MSP430F435 microcontroller, that communicates with the computer 204. In an embodiment, MCU 224 includes a processor, memory, clock, and I/O control unit. In an embodiment, the clock is a 32.768 kHz crystal, and 14 pF-18 pF capacitors are used to stabilize the crystal. MCU 210 controls communication between cap 208 and computer 204 via base station 206. Base station 206 includes an inductor 212 configured to receive data from MCU 210. Inductor 212 generates a magnetic field to be detected by a Hall Effect sensor 214 in cap 208. In an embodiment, an H-Bridge circuit governs the signal sent to inductor 212. It should be understood that while an exemplary embodiment of the present invention is directed to sending prescription dosage information to a wirelessly programmable cap using inductor 212, inductor 212 may be used to send any information to a receiver device over a short range communications link in accordance with embodiments of the present invention.

In an embodiment, base station 206 also includes one or more Light-emitting Diode(s) (LEDs) indicating that base station 206 is powered, one or more Liquid Crystal Display(s) (LCD) for displaying the state of the base station, a checksum for verification, and/or other base station information, and/or one or more speaker(s) providing an audible tone indicating completion of programming. However, it should be understood that LED(s), LCD(s), and speaker(s) are optional elements. For example, a base station for use in a pharmacy may include these elements, while a base station configured for home use may omit one or more of the above elements for further cost savings.

In an embodiment, both base station 206 and cap 208 include transponders (216 and 218) that control the wireless interface between cap 208 and base station 206. For example, transponders 216 and 218 may be implemented to enable communication from cap 208 to base station 206. In an embodiment, transponders 216 and 218 are Passive Low Frequency Interface Devices (PaLFi devices). In an embodiment, transponder 216 is used to program cap 208 with appropriate dosage interval information via loop antenna 220, and transponder 218 is used to relay compliance data back to base station 206 via chip antenna 222.

Information from transponder 218 and Hall Effect sensor 214 is relayed to an MCU 224 in cap 208. MCU 224 controls the cap timer, monitors opening and closing of the cap, and facilitates wireless communication of the cap with base station 206. Hall Effect sensor 214 is used to program cap 208 with appropriate dosage interval information. In an embodiment, cap 208 further includes a sensor 226 to detect when cap 208 is opened or closed. For example, in an embodiment, a switching mechanism is used to signal software running on cap 208 to record the current time and date. In an embodiment, the switching mechanism also resets the reminder system to arrange for the next dosage alert.

In an embodiment, MCU 224 outputs information to one or more LED(s) 228, speaker(s) 230, and/or LCD(s) 232. LED(s) 228 provide a visible alert when a dose is scheduled to be taken. In an embodiment, LED(s) 228 are integrated into LCD 232. LCD 232 displays the time until the next dose is scheduled to be taken and/or the time elapsed since the last dose was taken. Speaker(s) 230 provide an audible alert when a dose should be taken. For example, in an embodiment, an alarm system is activated when a dose is scheduled to be taken, and a piezoelectric buzzer and LED reminds the patient that it is time to take medication. In an embodiment, a battery (for example, a super capacitor) powers cap 208.

2.1 Prescription Dosage System

Figure 3:
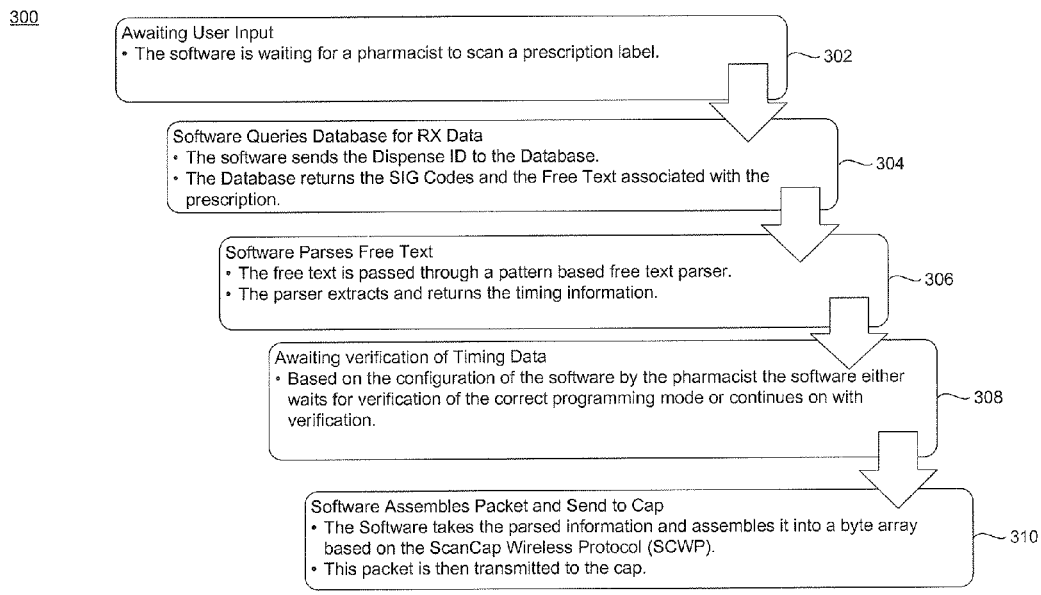
FIG. 3 depicts a flowchart of programming a cap in accordance with an embodiment of the present invention.

FIG. 3 depicts a flowchart 300 of programming a cap in accordance with an embodiment of the present invention. FIG. 3 will now be explained with reference to FIG. 2. In step 302, software running on computer 204 and/or base station 206 awaits user input. A prescription bottle is placed into (or near) base station 206. Base station 206 scans an identifier from the bottle (Dispense ID), which is sent to database 202 in step 304. Using the identifier, database 202 retrieves associated code(s) to write on the prescription label ("SIG codes") and any associated prescription text and returns this information to computer 204.

In step 306, software running on computer 204 and/or base station 206 parses the text (using, for example, a pattern based free text parser), which extracts timing information associated with the prescription.

In an embodiment, the software awaits verification of the timing data, as shown in step 308, by a user (e.g., a pharmacist). However, it should be noted that step 308 is optional. In step 310, the software running on computer 204 and/or base station 206 assembles the parsed information into a byte array and wirelessly transmits the information to cap 208. Advantageously, in an embodiment, this transfer is accomplished without the use of expensive equipment (such as Bluetooth) but rather uses an inexpensive transfer solution, such as a Hall Effect sensor. Exemplary embodiments of Hall Effect sensors are discussed in more detail later in this application.

Figure 4:
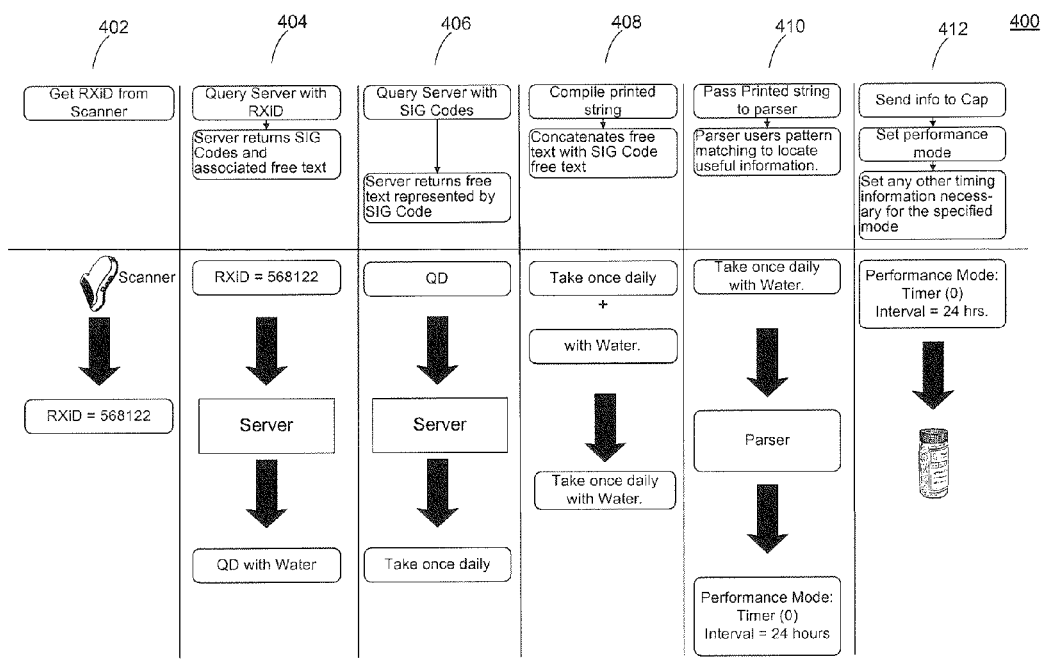
FIG. 4 depicts an exemplary method of parsing prescription information for a programmable cap in accordance with an embodiment of the present invention.

FIG. 4 depicts an exemplary method of parsing prescription information for a programmable cap in accordance with an embodiment of the present invention. In step 402 of FIG. 4, a prescription ID is received by a program when a prescription label is scanned. In step 404, a server is queried with the prescription ID, and the server returns SIG codes and associated free text. For example, the server may return "QD with Water" when the prescription ID "568122" is sent to the server as a query. In this example, the SIG code is "QD" and the associated text is "with Water." In an embodiment, SIG codes and free text are each stored in separate locations on the server, and the SIG codes and associated free text are returned separately. In another embodiment, SIG codes and free text are returned simultaneously, but SIG code information is labeled (or otherwise denoted) as SIG code information, and free text information is labeled (or otherwise denoted) as free text information. In another embodiment, SIG code information and free text information is returned simultaneously without any labeling or denotation of the information returned.

In step 406, the server is queried again to obtain a standard English translation for any SIG codes that were returned. For example, in an embodiment, the information returned in step 406 (SIG codes and associated clear text) is parsed using a SIG code recognition module, which identifies any SIG codes returned in the information by comparing the information against a list of known SIG codes. In an embodiment where SIG codes and free text are returned separately, the server is queried for each recognized SIG code to obtain the standard English translation, and the prescription information is concatenated when the SIG codes are translated. For example, the SIG code "QD" may be translated to "Take once daily." In step 408, a printed string is compiled by concatenating the translated SIG codes with the associated text. For example, the translated SIG code "Take once daily" is concatenated with the associated text "with Water" to form "Take once daily with Water."

In step 410, the printed string is passed to a parser to identify information used to program the cap. In an embodiment, the parser uses pattern matching to locate useful information. For example, the parser identifies the string "Take once daily" and uses it to configure the cap timer to set an alert for each 24 hours that elapses between doses. For example, the timer may be set to an initial value of "0" and the timing interval may be set for "24 hours." In step 412, a bit sequence is sent to the cap to program the cap.

Figure 5:
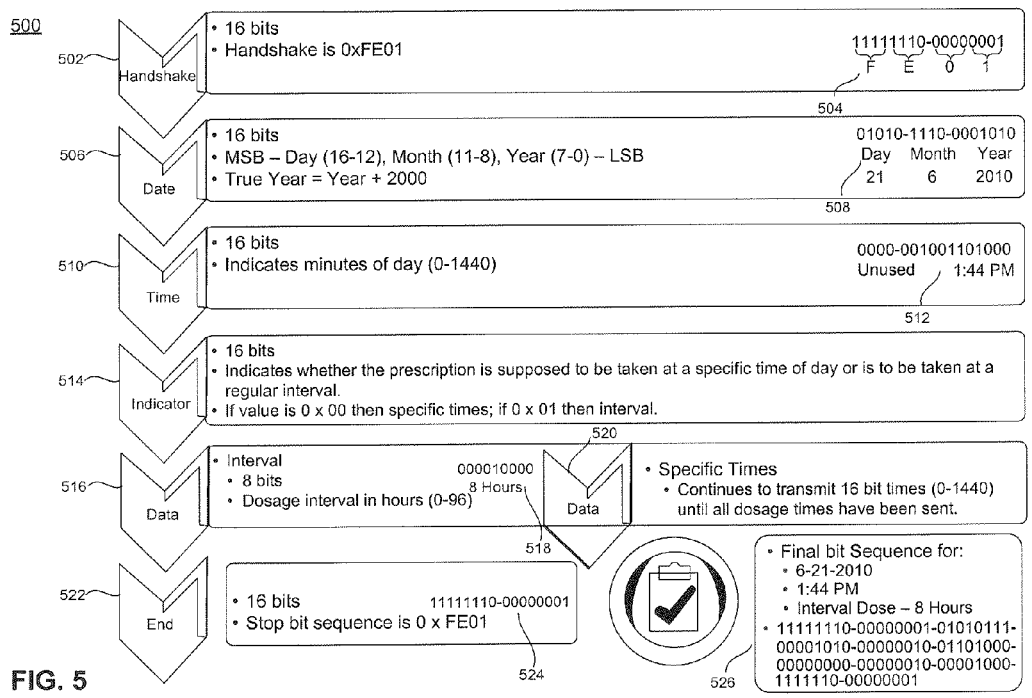
FIG. 5 depicts a flowchart of bit sequences used for programming a cap in accordance with an embodiment of the present invention.

FIG. 5 depicts a flowchart 500 of bit sequences used for programming a cap in accordance with an embodiment of the present invention. FIG. 5 will now be explained with reference to FIG. 2. In step 502, a handshake signal is sent from base station 206 to cap 208. In an embodiment, the handshake signal is a predetermined 16 bit sequence (for example, the bit sequence "FE01" 504). In step 506, information about the date of a scheduled dosage is sent to cap 208. In an embodiment, the data information is sent in a 16 bit message (for example, a number bits may be allocated 508 to the day, month, and year of the date). In step 510, information about the time of a scheduled first dosage is sent to cap 208. In an embodiment, the time information is sent in a 16 bit message (representing, for example, minutes of the day 512 to elapse before a dose is scheduled to be taken).

In step 514, an indicator message is sent to the cap containing information regarding whether the prescription should be taken at a specific time of day (for example, 1:44 pm) or at a regular interval (for example, every 8 hours). In an embodiment, a "0" bit may indicate that the prescription should be taken at a specific time, and a "1" bit may be used to indicate that the prescription should be taken at a regular interval. If the prescription is to be taken at a regular interval, the dosage interval is sent to cap 208 in step 516. In an embodiment, the dosage interval is sent using an 8 bit sequence specifying the interval in hours (0-96). For example, a "00001000" bit sequence indicates that the prescription should be taken every 8 hours. Alternatively, if the prescription is to be taken at specific time(s), one or more messages indicating the time(s) the prescription should be taken is sent to the cap 208 in step 520. In an embodiment, base station 206 continues to transmit 16 bit sequences to cap 208 until all dosage times have been sent (the time for the initial dose has already been sent in step 510). In an embodiment, each time sequence represents a minute of the day (from 0-1440, as there are 60 minutes in an hour, 24 hours in a day, and thus 1440 total minutes in a day). In step 522, a stop message is sent to cap 208. In an embodiment, the stop message is a predetermined 16 bit sequence (for example, a 16 bit sequence representing "FE01" 524.)

An exemplary bit sequence is shown in element 526 for programming cap 208 for dosages every 8 hours, starting at 1:44 pm, on Jun. 21, 2010. Exemplary bit sequence 526 includes a handshake, a date sequence, a start time sequence, an interval indicator, an interval sequence, and a stop sequence.

2.2 Hall Effect Data Transfer

Figure 6:
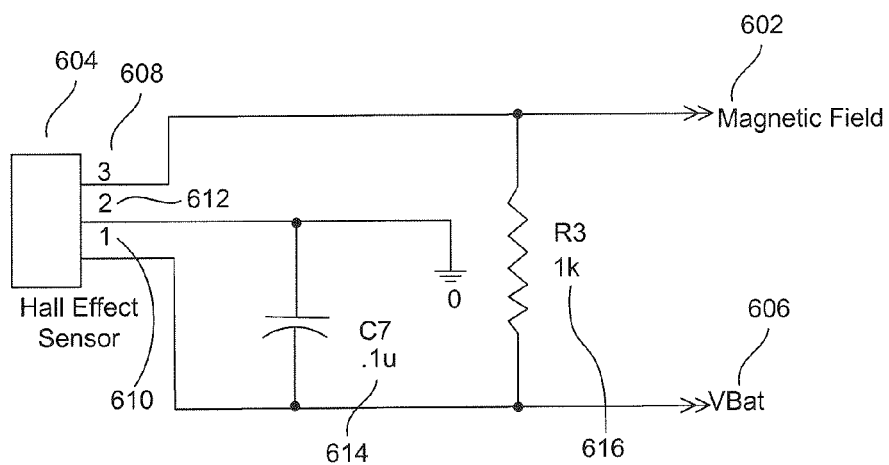
FIG. 6 is a diagram of a system incorporating a Hall Effect sensor in accordance with an embodiment of the present invention.

FIG. 6 is a diagram of a system 600 for detecting a change in a magnetic field 602 via a Hall Effect sensor 604 in accordance with an embodiment of the present invention. In an embodiment, Hall Effect sensor 604 is implemented as a transducer that varies its output voltage based on a change in magnetic field 602 generated by inductor 212 in base station 208.

In an embodiment, Hall Effect sensor 604 is powered using a battery 606 on the cap, and the voltage is input to pin 1 of the Hall Effect sensor 610. In an embodiment, pin 2 is grounded 612. In an embodiment, a capacitor 614 and a resistor 616 are included in the circuit design. It should be noted that while capacitor 614 is given a value of 0.1 uF and resistor 616 is given a value of 1 kΩ, these values are exemplary only.

In an embodiment, Hall Effect sensor 604 detects magnetic field 602 generated by inductor 212 via a pin 608. Hall Effect sensor 604 generates a "0" bit or a "1" bit depending on the direction of the detected magnetic field (e.g., "high" or "low"). This generated bit is then sent to the MCU's 224 Universal Asynchronous Receiver/Transmitter (UART) receive pin for decoding. In an embodiment, the UART controls the timing of decoding incoming bits. Each bit is maintained on the bus for a certain period of time, controlled by the UART. Proper synchronization of data transmission and reception ensures that the transmitter and receiver are transmitting and receiving data at the same rate. For example, if the data stream "111" is transmitted, the UART ensures that the received data stream is interpreted as "111" and not "11" or "1111." In an embodiment, a checksum is also used to confirm accurate transmission of data.

It should be understood that while an exemplary embodiment of the present invention is directed to receiving and decoding prescription dosage information at a wirelessly programmable cap using Hall Effect sensor 604, Hall Effect sensor 604 may be used to receive and decode any type of infatuation in accordance with embodiments of the present invention.

By using a Hall Effect sensor instead of a more expensive wireless data transfer system like Bluetooth, data is advantageously wirelessly transmitted from base station 206 to cap 208 while avoiding a high cost for equipment.

2.3 Programmable Cap

Figure 7A:
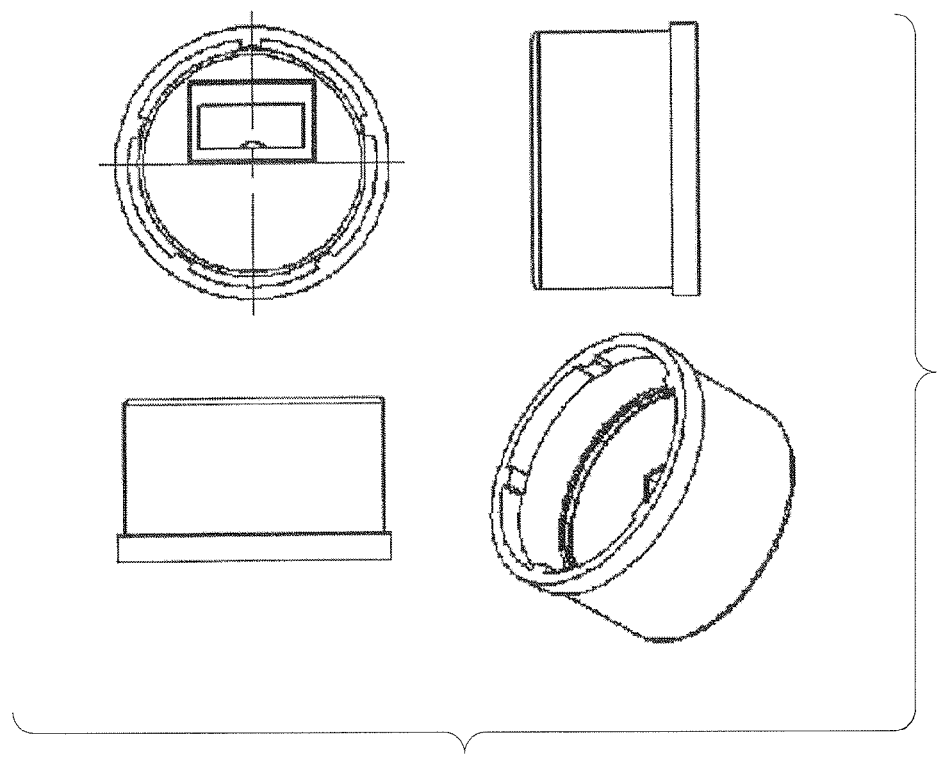
FIG. 7A shows different perspectives of a wirelessly programmable cap in accordance with an embodiment of the present invention.

FIG. 7A shows different perspectives of a wirelessly programmable cap in accordance with an embodiment of the present invention.

Figure 7B:
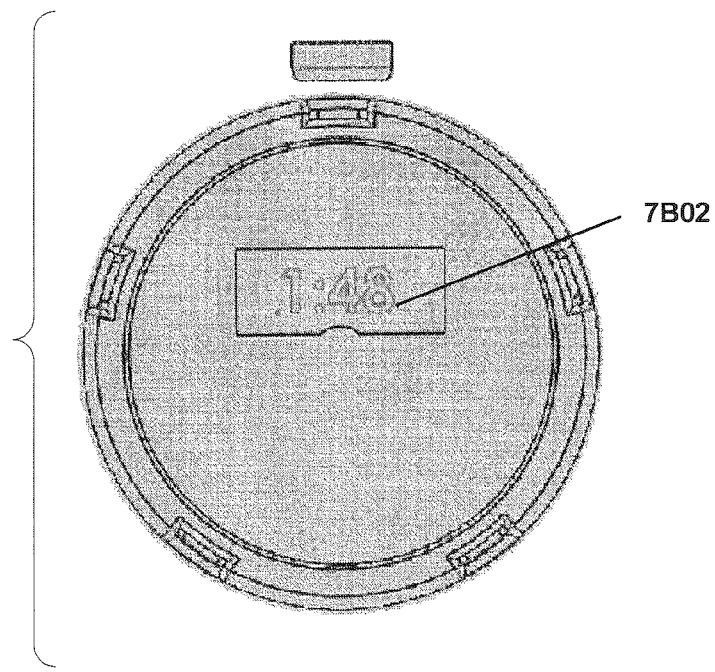
FIG. 7B shows a top view of a wirelessly programmable cap in accordance with an embodiment of the present invention.

FIG. 7B shows a top view of a wirelessly programmable cap in accordance with an embodiment of the present invention. In FIG. 7B, a dosage timer 7B02 is displayed on the cap.

3. Example

An example of the operation of a system in accordance with an embodiment of the present invention will now be discussed. A patient comes into the pharmacy with a prescription that needs to be filled. The pharmacist engages in his or her normal workflow entering the prescription into the computer and beginning to fill the order. However, instead of grabbing a normal safety cap when closing the bottle, the pharmacist grabs a wirelessly programmable cap in accordance with an embodiment of the present invention. The wirelessly programmable cap is placed on the prescription bottle.

The pharmacist walks over to the programming station and scans the barcode on the label. In an embodiment, the software might prompt the pharmacist to verify the timing information being sent to the cap. If the system does prompt the pharmacist, he or she confirms the settings and then waves the cap through the programming space. This space is either under or near the base station. In an embodiment, a checksum is displayed on the screen and on the cap, and the pharmacist verifies these two numbers against each other. If the numbers match, then the cap was programmed successfully according to dosage information provided by the physician. There are no additional steps for the pharmacist to take other than to dispense the filled prescription as normal.

The patient picks up his or her prescription from the pharmacy. In an embodiment, the cap is in 1 of 3 performance modes: (1) Interval Dosage Mode; (2) Specifically Timed Dosage Mode; or (3) Stopwatch Mode. For example, in an Interval Dosage Mode set for every 6 hours, the cap awaits the patient to take his or her first dose. After the patient has taken the first dose, the display on the cap begins counting down from 6 hours. This shows the patient how long until the next dose is scheduled. When the time for the next dose arrives, the speaker and/or the LED on the cap begin pulse on and off (i.e., for 30 seconds) to alert the patient to take medication. If the patient fails to open the cap within the first 30 seconds, the cap goes silent. The cap will flash and beep for 3 seconds every minute to continue to alert the patient that medication is due. If at any time the patient opens the cap, the alerts will stop, and the timer will be reset to alert the patient in another 6 hours.

In an cap set for Specifically Timed Dosage Mode (e.g., "Take with breakfast and with dinner"), the cap will alert the patient when a programmed time occurs. For example, assuming that the patient filled the prescription around noon, the cap would remain in countdown mode showing the time until the next dose scheduled to be taken at dinnertime. When the time for the next dose arrives, the speaker and/or the LED on the cap pulse on and off to alert the patient to take medication. If the patient fails to open the cap within the first 30 seconds, the cap goes silent. The cap will flash and beep for 3 seconds every minute for ⅓ the time between the current dose and the next dosage time to continue to alert the patient that medication is due to be taken. If at any time the patient opens the cap, the alerts will stop, and the timer will be reset to alert the patient when the next dose is due.

In a cap set for Stopwatch Mode (e.g., "Take As Directed"), the Cap does not notify the patient of when to take the next dose. Rather, it simply shows the patient how long it has been since the last dose was taken. The patient takes medication as prescribed for the remainder of the prescription period. If the patient runs out of medication, the patient (or pharmacist) may place the cap in a base station, located at either the patient's home or at the pharmacy, and the data may be uploaded from the cap to an interne server that allows relevant medical professionals to see the patient's compliance data. The cap may then be removed from the bottle to prevent additional warnings and can either be disposed of or recycled by returning it to the pharmacist.

4. Conclusion

The above systems and methods may be implemented as a computer program executing on a machine, as a computer program product, or as a tangible and/or non-transitory computer-readable medium having stored instructions.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A system, comprising:
  a computer, wherein the computer is configured to:
    receive a prescription identifier scanned from a prescription vial,
    send a request to a pharmacy records database storing a plurality of prescriptions for a prescription message corresponding to the prescription identifier,
    receive the prescription message from the pharmacy records database,
    parse a SIG code from the prescription message,
    obtain a translation of the SIG code into a language,
    determine a free text portion corresponding to the SIG code,
    concatenate the translated SIG code with the free text portion to produce a concatenated string,
    send the concatenated string to a parser,
    perform, using the parser, pattern matching on the concatenated string,
    determine, based on the pattern matching, programming information to configure a timer to send an alert at a time designated by the programming information, and
    initiate a transmission of the programming information; and
  a wirelessly programmable prescription bottle cap, comprising:

a first sensor configured to wirelessly receive the programming information, and
a control unit comprising:
a memory configured to store the programming information, and
a processor configured to set the timer and to instruct the wirelessly programmable prescription bottle cap to send the alert at the time designated by the programming information.

2. The system of claim 1, wherein the first sensor is a Hall Effect sensor.

3. The system of claim 1, wherein the first sensor is configured to output a 1 or a 0 to the control unit based on a direction of a detected magnetic field.

4. The system of claim 1, wherein the wirelessly programmable prescription bottle cap further comprises:
a second sensor configured to send a message to the control unit when the wirelessly programmable prescription bottle cap is opened.

5. The system of claim 4, wherein the control unit is configured to terminate generation of the alert after receiving the message.

6. The system of claim 4, wherein the control unit is configured to reset the dosage timer after receiving the message.

7. The system of claim 1, wherein the wirelessly programmable prescription bottle cap further comprises:
the timer, wherein the timer is configured to monitor the time designated by the programming information; and
a switching mechanism configured to:
inform the processor when the wirelessly programmable prescription bottle cap is opened, and
initiate resetting of the timer.

8. The system of claim 1, wherein the wirelessly programmable prescription bottle cap further comprises:
a display configured to display a time until a dose of medication is scheduled to be taken.

9. The system of claim 1, further comprising:
a display configured to display an elapsed time since a dosage was taken.

10. A method comprising:
receiving, using a processing device, a prescription identifier;
sending, using the processing device, a request to a prescription database storing a plurality of prescriptions for a prescription message corresponding to the prescription identifier;
parsing, using the processing device, prescription dosage information from the prescription message;
parsing a SIG code from the prescription message;
obtaining a translation of the SIG code into a language;
determining a free text portion corresponding to the SIG code;
concatenating the translated SIG code with the free text portion to produce a concatenated string;
sending the concatenated string to a parser;
performing, using the parser, pattern matching on the concatenated string;
determining, based on the pattern matching, programming information to configure a timer to send an alert at a time designated by the programming information;
establishing, using the processing device, communications with a wirelessly programmable prescription bottle cap; and
sending, using the processing device, the programming information to the wirelessly programmable prescription bottle cap.

11. A non-transitory computer-readable medium having instructions stored thereon that, when executed by a computing device, cause the computing device to perform operations comprising:
receiving a prescription identifier;
sending a request to a prescription database storing a plurality of prescriptions for a prescription message corresponding to the prescription identifier;
parsing prescription dosage information from the prescription message;
parsing a SIG code from the prescription message;
obtaining a translation of the SIG code into a language;
determining a free text portion corresponding to the SIG code;
concatenating the translated SIG code with the free text portion to produce a concatenated string;
sending the concatenated string to a parser;
performing, using the parser, pattern matching on the concatenated string;
determining, based on the pattern matching, programming information to configure a timer to send an alert at a time designated by the programming information;
establishing communications with a wirelessly programmable prescription bottle cap; and
sending the programming information to the wirelessly programmable prescription bottle cap.

12. A system comprising:
a computer at a pharmacy, wherein the computer is configured to:
receive a prescription identifier scanned from a prescription vial presented by a user at the pharmacy,
send a request to a pharmacy records database storing a plurality of prescriptions for a prescription message corresponding to the prescription identifier,
receive the prescription message from the pharmacy records database,
parse a SIG code from the prescription message,
obtain a translation of the SIG code into a language,
determine a free text portion corresponding to the SIG code,
concatenate the translated SIG code with the free text portion to produce a concatenated string,
send the concatenated string to a parser,
perform, using the parser, pattern matching on the concatenated string,
determine, based on the pattern matching, programming information to configure a timer to send an alert at a time designated by the programming information, and
initiate a transmission of the programming information;
a base station at the pharmacy, wherein the base station is in communication with the computer, and wherein the base station is configured to:
receive the programming information,
establish a short range wireless link, and
initiate a transmission of a wireless signal over the short range wireless link, wherein the signal contains the programming information; and
a wirelessly programmable prescription bottle cap comprising:
a sensor configured to:
detect the wireless signal, and
generate the programming information based on the wireless signal; and a control unit configured to set the timer and to program the wirelessly programmable prescription bottle cap to send the alert at the time designated by the programming information.

13. The system of claim 12, wherein the sensor is a Hall Effect sensor configured to generate a bit string representative of the programming information based on a magnetic field.

14. The system of claim 12, wherein the base station further comprises:
   a light-emitting diode (LED); and
   a liquid crystal display (LCD).

15. The system of claim 12, wherein the wirelessly programmable prescription bottle cap further comprises:
   a speaker configured to provide an audible tone to send the alert.

16. The system of claim 12, wherein the base station further comprises:
   a transponder configured to receive compliance data from the wirelessly programmable prescription bottle cap.

17. The method of claim 10, wherein establishing communications with the wirelessly programmable prescription bottle cap comprises establishing a short range wireless link with the wirelessly programmable prescription bottle cap.

18. The system of claim 12, wherein the control unit of the wirelessly programmable prescription bottle cap is further configured to initiate a transmission, based on the programming information, of a text message to be sent from the control unit to a portable communications device of a patient when a dosage is scheduled to be taken by the patient.

19. The system of claim 12, wherein the computer is further configured to continuously initiate transmissions of wireless signals over the short range wireless link until all dosage times for the prescription message have been sent to the wirelessly programmable prescription bottle cap.

20. The system of claim 12, wherein the programming information includes:
   a date;
   a start time;
   an interval indicator; and
   an interval.

* * * * *